United States Patent
Waller et al.

(10) Patent No.: US 8,506,477 B2
(45) Date of Patent: Aug. 13, 2013

(54) SYSTEM AND METHOD FOR ENDOSCOPIC TREATMENT OF TISSUE

(75) Inventors: David F. Waller, Tampa, FL (US); Hilbert D. Brown, Winston-Salem, NC (US); Patricia J. Chilton, Pilot Mountain, NC (US); David M. Hardin, Winston-Salem, NC (US); Kimberly K. Ingram, Rural Hall, NC (US); Kenneth C. Kennedy, II, Clemmons, NC (US); Vihar C. Surti, Winston-Salem, NC (US); Marcie G. Yount, Pilot Mountain, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1121 days.

(21) Appl. No.: 11/888,216

(22) Filed: Jul. 31, 2007

(65) Prior Publication Data

US 2008/0108874 A1 May 8, 2008

Related U.S. Application Data

(60) Provisional application No. 60/834,776, filed on Aug. 1, 2006.

(51) Int. Cl.
*A61B 1/00* (2006.01)
*A61B 1/04* (2006.01)

(52) U.S. Cl.
USPC .............................. 600/127; 600/104; 600/129

(58) Field of Classification Search
USPC .................. 600/104, 127, 129, 175, 121–125; 606/138, 140
See application file for complete search history.

(56) References Cited

U.S. PATENT DOCUMENTS

| | | | |
|---|---|---|---|
| 4,735,194 A | 4/1988 | Stiegmann | 128/6 |
| 5,269,789 A | 12/1993 | Chin et al. | 606/140 |
| 5,320,630 A | 6/1994 | Ahmed | 606/140 |
| 5,389,084 A * | 2/1995 | Horan et al. | 604/192 |
| 5,398,844 A * | 3/1995 | Zaslavsky et al. | 221/208 |
| 5,423,834 A | 6/1995 | Ahmed | 606/140 |
| 5,462,559 A | 10/1995 | Ahmed | 606/140 |
| 5,624,453 A | 4/1997 | Ahmed | 606/140 |
| 5,725,475 A * | 3/1998 | Yasui et al. | 600/127 |
| 5,735,861 A | 4/1998 | Peifer et al. | 606/139 |
| 6,007,551 A | 12/1999 | Peifer et al. | 606/140 |
| 6,059,719 A * | 5/2000 | Yamamoto et al. | 600/127 |
| 6,149,659 A | 11/2000 | Ahmed | 606/140 |
| 6,565,578 B1 | 5/2003 | Peifer et al. | 606/139 |
| 7,204,804 B2 * | 4/2007 | Zirps et al. | 600/127 |
| 7,819,840 B2 * | 10/2010 | Burnside et al. | 604/101.01 |
| 2002/0035311 A1 * | 3/2002 | Ouchi | 600/175 |
| 2002/0177847 A1 * | 11/2002 | Long | 606/46 |
| 2004/0006256 A1 | 1/2004 | Suzuki et al. | 600/140 |
| 2005/0137453 A1 * | 6/2005 | Ouchi et al. | 600/106 |
| 2006/0282088 A1 * | 12/2006 | Ryan | 606/144 |

FOREIGN PATENT DOCUMENTS

| | | |
|---|---|---|
| EP | 0 679 368 A | 11/2005 |
| JP | 10-501165 | 3/1998 |
| JP | 10-295624 | 11/1998 |
| JP | 11-244219 | 9/1999 |
| JP | 2002-000545 | 1/2002 |
| JP | 2002-017665 | 1/2002 |
| JP | 2003-339618 | 12/2003 |
| WO | WO 95/34244 | 1/1995 |

* cited by examiner

*Primary Examiner* — Alireza Nia
(74) *Attorney, Agent, or Firm* — Brinks Hofer Gilson & Lione

(57) ABSTRACT

An improved ligating system with a ligating barrel having an adjustable diameter for use with endoscopes of varying sizes is disclosed. The adjustable diameter may be provided by a collet, a flexible helical band, a plurality of screws, or a tapered elastomeric section.

9 Claims, 6 Drawing Sheets

SYSTEM AND METHOD FOR ENDOSCOPIC TREATMENT OF TISSUE

CROSS REFERENCE TO RELATED APPLICATION

The present application claims the benefit of U.S. Provisional Patent Application Ser. No. 60/834,776, filed Aug. 1, 2006, incorporated by reference herein in its entirety.

TECHNICAL FIELD

This system is related to improved medical devices for the endoscopic treatment of tissue.

BACKGROUND OF THE INVENTION

Throughout this specification, when discussing the application of this invention in relation to a surgeon using an endoscope, the term "distal" with respect to the ligation barrel, is intended to refer to a location that is situated away from the surgeon. The term "proximal" is intended to refer to a location that is near the surgeon and nearer to the surgeon than a point distal to the surgeon.

The treatment of tissue encompasses a variety of techniques such as electrocauterization, heat therapy, resection (removal of tissue), and sclerotherapy (the injection of medicine into target tissue). These treatment techniques usually involve the passing of medical instruments through the operating channel of the endoscope. The endoscope permits minimally invasive access as well as visualization and suction aids.

Another technique that frequently utilizes the operating channel of the endoscope is ligation, which involves applying a band or ligature around a vessel or portion of tissue, thereby cutting off blood or fluid flow and causing the tissue to necrose and separate from adjacent healthy tissue. Ligation is widely used to treat a number of medical tissue conditions, including, but not limited to, hemorrhoids, polyps, ballooning varices, and other types of lesions, including those that are cancerous. Typically, ligators are also used with a suction or vacuum means to draw the tissue into the distal tip, whereby the band is deployed over the base of the diseased tissue to cut off blood flow. The ligating device is typically activated by retracting a line (string, wire, or cable) that is attached to the ligator at the distal end of an endoscope and is threaded through the operating channel of the endoscope to the proximal end of the instrument. The ligator can be activated by mechanically pulling the activating line by means of a hand-operated reel or trigger, or a motor drive mechanism. Various other ligating devices use cooperating inner and outer members that slide the individual bands by pushing or pulling them from the tip of the inner or outer member, the bands being preloaded onto the inner or outer member prior to deployment.

To prevent having to withdraw the instrument from the patient, reload, and reintroduce it for treating additional tissue or vessels, devices have been developed that are capable of sequentially delivering multiple preloaded bands, thus shortening the procedure time and improving patient comfort. Multiple band ligating devices include designs that individually tether or otherwise secure the bands to the dispenser and then release them sequentially as needed, often by use of one or more strings extending to the proximal end.

It is often desirable to combine another endoscopic procedure with band ligation, such as sclerotherapy or tissue removal with a surgical snare. However, while the operating channel of the endoscope is often large enough to accommodate more than just an activating line from a ligator, combining the medical instruments necessary for the second procedure with the ligator can be problematic. Thus, there is a need for a ligating device that can be combined with other medical instruments in endoscopic procedures.

Band ligators are generally provided in multiple sizes to fit various scope diameters. The ligators sometimes have an internal ridge that acts as a positive stop to prevent the endoscopic cap from sliding proximally down the scope. This is made possible because the ridge has a smaller diameter than the diameter of the scope. The same ligator usually cannot be used on another endoscope having a different diameter. If the ligator is too big, when placed onto an endoscope of differing diameter, there is a risk that the tabs will obstruct the features usually found in the cap of an endoscope: the light source, working channel, and camera lens. A ligator that is too small will likely not fit securely over the cap of the endoscope. Thus, there is a need for a band ligator barrel that can accommodate endoscopes of varying diameters without obstructing the endoscope cap features.

BRIEF SUMMARY

The present invention provides a system and method for endoscopic treatment of tissue. In particular, a system is provided for use in an endoscope having an operating channel. The system includes a ligating system having an activating component and a ligating barrel. The system further includes a medical instrument having an elongate shaft and an operating member disposed near the distal end thereof. The activating component includes a mounting component having a first threading channel that fits into the working channel of the endoscope. In one preferred aspect of the invention, the first threading channel of the mounting component has a diameter of at least 2.5 millimeters, and more preferably a diameter of about 3.2 millimeters. The ligating barrel fits onto a distal end of the endoscope and is operably connected to the activating component. The shaft of the medical instrument is disposed through the first threading channel, the operating channel, and the ligating barrel so as to position the operating member near the tissue to be treated.

In another aspect, the present invention provides a system useful for convenient endoscopic resection of tissue. The system includes an endoscope having an operating channel and a ligating barrel extending from the channel. The ligating barrel includes at least one, and desirably multiple, ligating bands disposed thereon and deployable therefrom. An elongated tissue resection device extends through the working channel and is effective to resect tissue captured by the bands. In certain embodiments, the tissue resection device is an electrosurgical snare.

In another aspect, the invention provides a method for endoscopically resecting tissue. The method includes advancing an endoscope into a body passageway of a patient. The endoscope has an operating channel and a ligating barrel extending from the channel. The patient's tissue is drawn into the ligating barrel and a ligating band is deployed to form a ligated tissue mass or pseudo-polyp. An elongated tissue resecting device, such as an electrosurgical snare, is advanced through the operating channel of the endoscope, and is used to resect the ligated tissue mass.

The improved ligating barrels of the present invention comprise a band deployment section and a conformable section. Generally, the conformable section has a means for adjusting the interior diameter of the conformable section to accommodate attachment to the distal end of an endoscope.

Any structure having this ability is considered an embodiment of this invention. For example, in one particular embodiment, the conformable section comprises a rigid first section having a fixed internal diameter, at least two tabs that provide a decreased diameter, and, adapted to contain with its lumen, the distal end of an endoscope. There is a tapered elastomeric second section having an expandable diameter with internal ribbing that provides a friction fit for the distal end of the endoscope.

In another embodiment, the conformable section comprises a collet having a first end with a maximum diameter and a second end with an adjustable diameter. There is at least one slit at least partially along the length of the conformable section. The first end is adjacent to the band deployment section and the second end is spaced away from and proximal the band deployment section. There is also a ring rotatably disposed about the collet, wherein rotation of said ring relative to the collet changes the diameter of the second end.

In another embodiment, the conformable section comprises a flexible helical band configured for attachment to an endoscope. The band has a distal end in communication with the band deployment section. There is also a proximate end proximal to the band deployment section. The distal end has a fixed diameter and the proximate end has an adjustable diameter.

In yet another embodiment, the conformable section comprises a plurality of screws spaced around the circumference of the conformable section to adjust the inner diameter of the conformable section. The screws are configured to engage an endoscope to secure the ligating barrel. Some embodiments have the screws spaced equidistant around the circumference of the conformable section.

The embodiments of the presenting invention may further comprise an endoscope with a distal end and a proximal portion with the ligating barrel disposed on the distal end and an activating component disposed on the proximal portion of the endoscope, the activating component being operably connected to the ligating barrel.

These and other features of the invention will become apparent upon review of the following detailed description of the presently preferred embodiments of the invention, taken into conjunction with the appended figures.

DETAILED DESCRIPTION OF THE DRAWINGS AND THE PRESENTLY PREFERRED EMBODIMENTS

Figure 1:
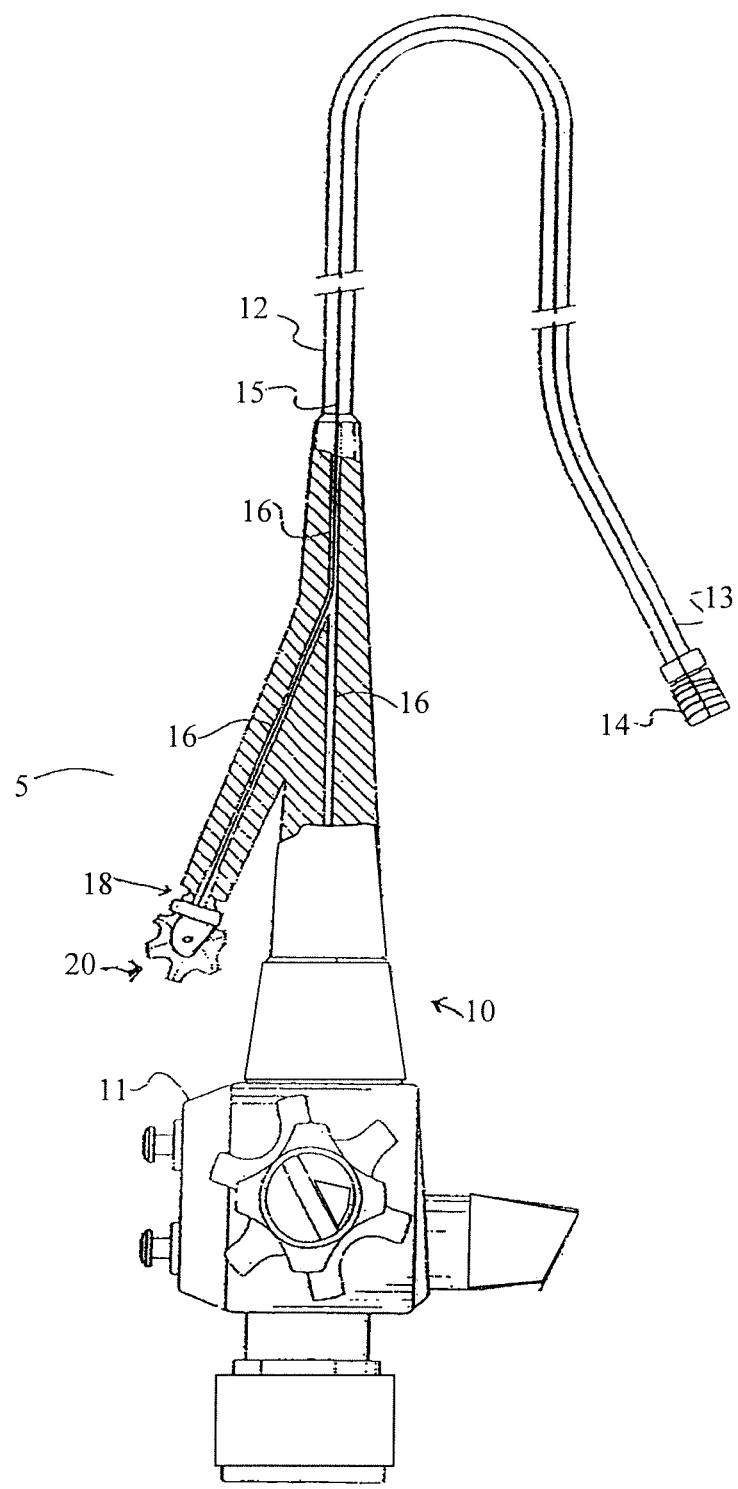
FIG. 1 is a longitudinal fragmented view of an endoscope with a conventional ligating system.

Referring now to the drawings, there is shown in FIG. 1 a conventional ligating system 5 with an endoscope 10. The endoscope 10 is a conventional endoscope with an activating component 11 disposed on the proximal portion of the endoscope, a flexible section 12, and a distal end portion 13. The ligating system 5 has a ligating barrel 14 attached to the distal end of an endoscope 10. An activating component 11 is operably connected to the ligating barrel 14. The ligating barrel 14 and actuating component are generally shown in FIG. 1. A more detailed description of the barrel 14 and activating component is provided in U.S. Pat. No. 5,624,453, which disclosure is hereby incorporated by reference. U.S. Patent Publication No. 2006-0089660 A1, hereby incorporated by reference, also provides a description of a ligating barrel that may be used in embodiments of the present invention.

The ligating barrel 14 is disposed on a distal end portion 13 of endoscope 10 and includes an activation line 15. The endoscope 10 also includes a working channel 16 which extends through the endoscope 10 from the ligating barrel 14 to both the activating component 11 and to the proximal opening 18. The activation line 15 is threaded from the ligating barrel 14 through the working channel 16 and exits through the proximal opening 18. The ligating barrel 14 is preferably of a hard plastic clear polycarbonate for maximum durability and visibility. The activation line 15 operably connects the activating component 11 and the ligating barrel 14. One or more ligating bands 25 may be removably disposed about the ligating barrel 14. The ligating bands 25 may be operably coupled to the activating component 11 via the activation line 15, and further wherein operation of the activating component 11 releases one or more ligating bands 25 from the ligating barrel 14. There may be six or more deployable ligating bands 25 disposed on the ligating barrel 14.

Other medical instruments, such as an electrosurgical snare, may be used with conventional ligating systems as well as with the ligating barrels of the present invention. Such medical instruments may be disposed through a working channel 16 of the endoscope. The electrosurgical snare may be made from a braided stainless steel cable and having a hexagonal shape when in the open configuration. The braided stainless steel cable provides the operating loop with a combination of flexibility, strength and resiliency that permits multiple resections of tissue. A suitable surgical snare system is the 7FR Soft AcuSnare™ Mini Hexagonal Head disposable polypectomy snare, sold by Wilson-Cook Medical Inc., d/b/a Cook™ Endoscopy, 4900 Bethania Station Road, Winston-Salem, N.C. 27105, catalog no. SASMH-1. The 7FR Soft AcuSnare™ Mini Hexagonal Head disposable polypectomy snare has a braided stainless steel snare with a loop size of 1.5 cm×2.5 cm and a catheter sheath size of 7.0 FR. Although other types of surgical snare systems (or other types of medical catheter devices) may be utilized in combination with the ligating system 5 disclosed herein, these other devices may not be as suitable or efficient for performing multiple tissue resections.

The improved ligating barrel 114 of the present invention comprises a band deployment section 20 and a conformable section. The conformable section has means of adjusting the interior diameter of the conformable section for attachment to the distal end of an endoscope. As further described below and seen in FIGS. 2-5B, the adjustment means can comprise a variety of structures including a collet 35, a flexible helical band 55, or a plurality of screws 75. In some embodiments, the means comprises a flexible elastomeric section 90 with internal ribbing 95 that provides a friction fit for the distal end portion 13 of an endoscope. The internal ribbing is disposed circumferentially about an interior surface of the second section. The internal ribbing may comprise a plurality of spaced apart ribs in some embodiments.

The improved ligating barrels and systems are capable of being used on endoscopes of varying diameters. Preferably, the ligating barrels and systems of the present invention can be used with endoscopes having outer diameters ranging from about 4 mm to about 16 mm. Some embodiments can be used with an endoscope having outer diameters ranging from about 8 mm to about 12 mm, or about 12 mm to about 16 mm. More preferably, the barrels can be used on endoscopes with outer diameters ranging from about 8.6 mm to about 11.5 mm. The barrels fit securely around the distal tip of an endoscope affording the operator reduced apprehension of dislodgement.

Figure 2A:
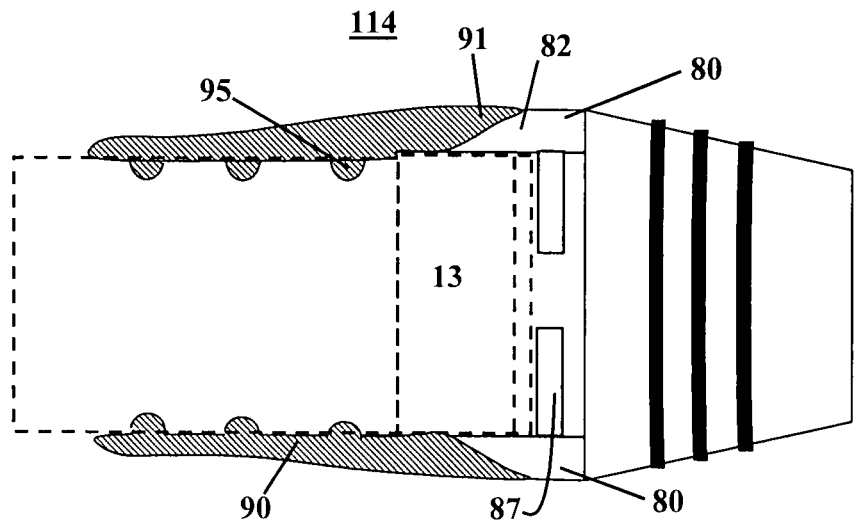
FIG. 2A shows a ligating barrel of the present invention attached to the distal end of an endoscope fitted over the cap of an endoscope.
Figure 2B:
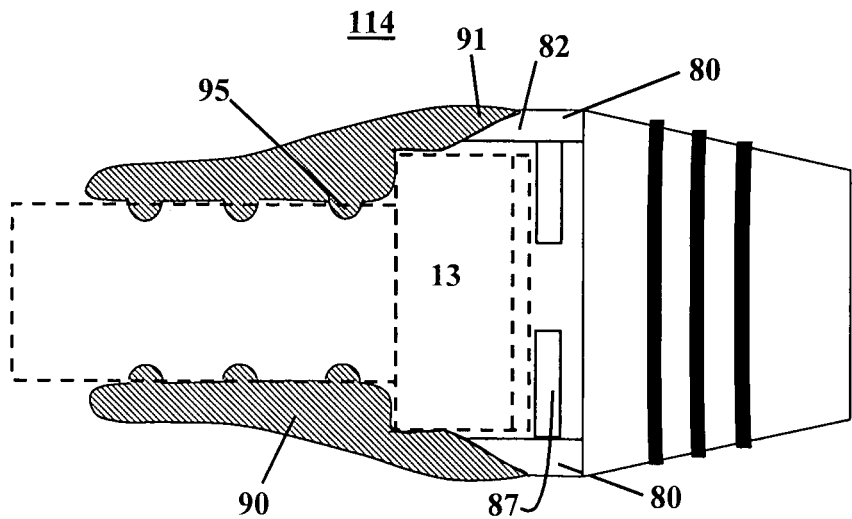
FIG. 2B shows the ligating barrel conforming to fit over an endoscope with a smaller outer diameter.

One embodiment of a ligating barrel 114 shown in FIG. 2 comprises a band deployment section 20 and a conformable section 30. The band deployment section 20 is functionally and structurally similar or identical to that of the conventional barrel disclosed in U.S. Pat. No. 5,624,453. FIG. 2 shows an embodiment having a rigid first section 80 with a fixed internal diameter adapted to contain within its lumen the distal end portion 13 of an endoscope. The first section 80 has at least two tabs 87 that provide a decreased inner diameter. The tabs 87 act as stops that prevent the ligating barrel 114 from sliding proximally down the scope. The tabs 87 also control how much volume the ligating barrel 114 has for suctioning. The tabs 87 are configured so as to not interfere with the light source, working channel, or camera lens of the endoscope.

The first section 80 is rigid molded to a tapered elastomeric second section 90 having an expandable diameter with internal ribbing 95 that provides a friction fit for the distal end portion 13 of the endoscope. The distal end 91 of the second section 90 is in communication with the first section 80. The internal diameter of the second section 90 is adjustable by actuating or press fitting the second section 90 onto the distal end portion 13 of the endoscope to approximate the outer diameter of an endoscope. The second section 90 is preferably made of Latex, Polyisoprene, Santoprene, Silicone, Tecoflex, Neoprene, or any non-toxic elastomer. Also preferable are elastomers that have about 50 A to about 100 A Shore A durometer or, in some embodiments, about 60 A to about 90 A in other embodiments. The second section can also have an elongation of about 90% to about 500% or any combination or subcombination therein.

The elastomeric second section 90 is capable of stretching to fit smaller and larger endoscopes. The internal ribbing 95 allows a physician to fully seat the distal end portion 13 of the endoscope in the ligating barrel 114 by press fitting the barrel 114 onto the distal end portion 13 of the endoscope. This action increases the adjustable diameter of the second section 90.

Figure 3:
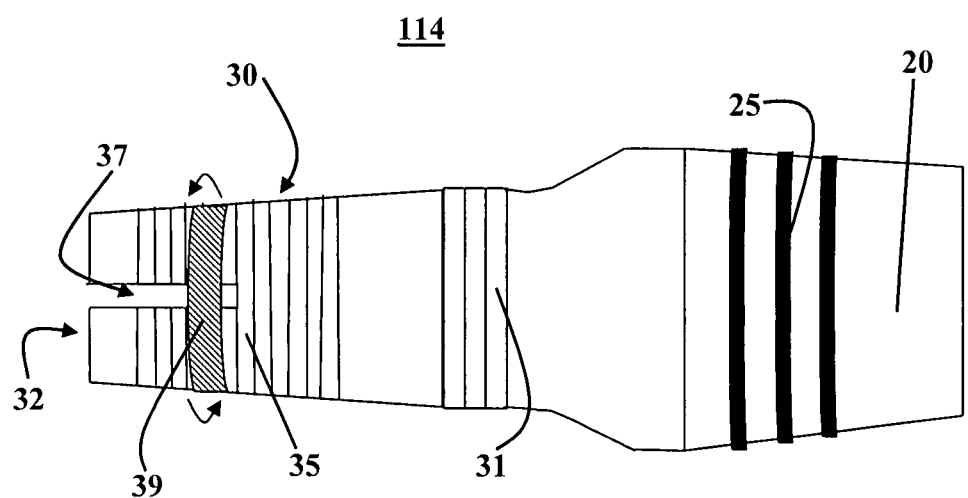
FIG. 3 is a plan view of a ligating barrel with a collet and the conformable section having a threaded ring.

Another example of the improved ligating barrel of the present invention is shown in FIG. 3 where the conformable section 30 comprises an externally threaded collet 35 having a first end 31 with a maximum diameter and a second end 32 with an adjustable diameter. At least one slit 37 extends at least partially along the length of the conformable section. The first end 31 of the conformable section 30 is spaced away from and adjacent to the band deployment section 20 and the second end 32 is proximal to the band deployment section 20. A ring 39 is rotatably disposed about the collet 35 such that rotation of the ring relative to the collet changes the diameter of the second end 32. This embodiment may also have internal tabs (not shown) to prevent the ligating barrel from sliding proximally down the scope.

A user adjusts the diameter near the second end 32 of the collet 35 by actuating or rotating the threaded ring 39. Rotating the ring 39 in a clockwise fashion, for instance, tightens the collet 35 and decreases the adjustable diameter to approximate the diameter of an endoscope having an outer diameter less than the maximum diameter of the first end 31. Rotating the ring 39 in a counter-clockwise fashion to bring the ring 39 closer to the first end 31 yields a diameter approaching the maximum diameter of the first end 31. Alternatively, a slide band (not shown) having a friction fit may be placed over a collet having no threads. Sliding the band toward the second end of the collet tightens the collet and yields a smaller diameter. Sliding the band toward the first end of the collet loosens the collet and provides a diameter approaching that of the first end.

Figure 4:
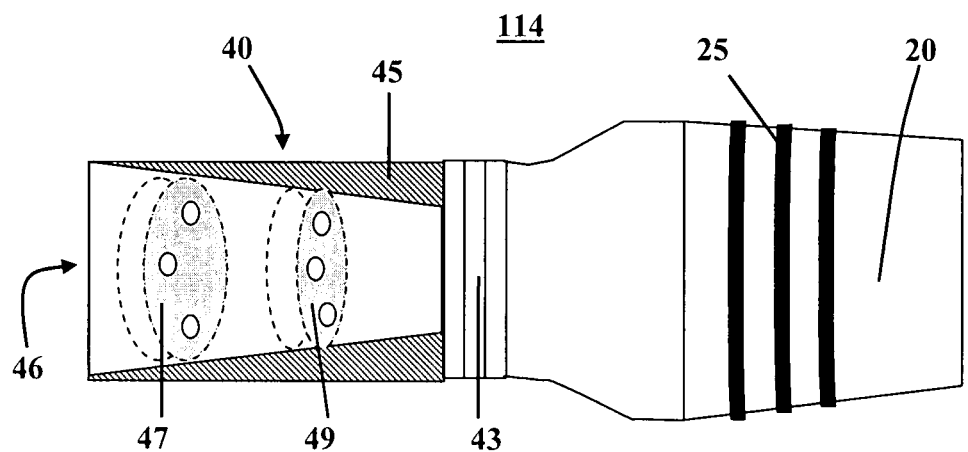
FIG. 4 is a partial sectional view of the conformable section with conformable walls.

In another embodiment, the conformable section 40 has a tapered interior surface as shown in FIG. 4. There is a first end 43 with an inner diameter that is smaller than the inner diameter of the second end 46. The conformable wall 45 of the conformable section 40, therefore, narrows as it comes into contact with the distal end portion 13 of an endoscope having varying sizes. A range of scopes from about 5 mm to about 13 mm can fit within the conformable section 40. A large diameter endoscope 47 contacts the conformable wall 45 at points near adjacent to the second end 46. A small diameter scope 49 contacts the conformable wall 45 at points near adjacent the first end 43.

Figure 5A:
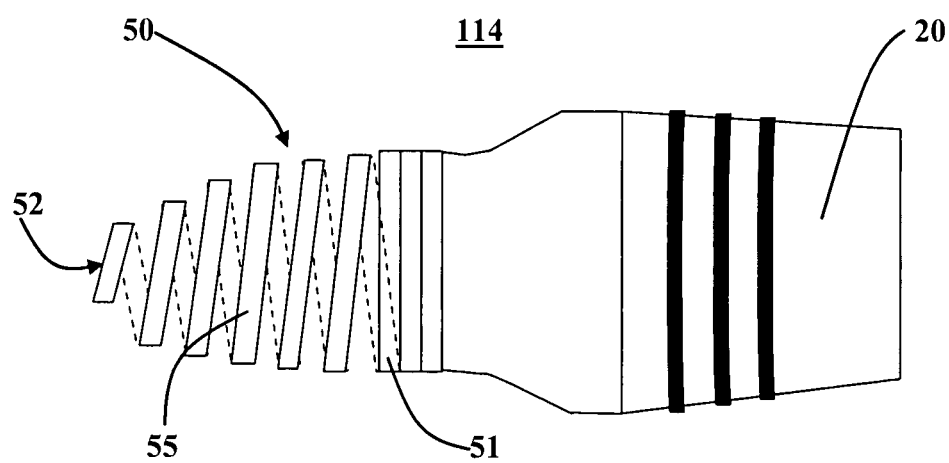
FIG. 5A is a plan view of an embodiment of the present invention with a helical band on the conformable section.

FIG. 5A shows an example of an improved ligating barrel 114 where the conformable section 50 comprises a flexible helical band 55 that is configured for attachment to an endoscope. The helical band 55 has a distal end 51 in communication with the band deployment section 20 and a proximate end 52 that is proximal to and spaced away from the band deployment section 20. The distal end 51 has a fixed diameter and the proximate end 52 has an adjustable diameter. The helical band 55 wraps around the endoscope and conforms to the endoscope's outer diameter with sufficient gripping force to secure the ligating barrel 114 thereto. The helical band 55 has the structure of a helix and therefore has a number of turns. When the helical band 55 is wrapped around an endoscope having a diameter that approximates the diameter of the distal end 51, the number of turns decreases. The number of turns increases when the helical band 55 adjusts to fit around an endoscope having a diameter that is less than the diameter of the distal end 51 of the helical band 55.

The helical band 55 may be constructed of an elastomeric material that may have metal embedded enforcement. Such metallic enforcement includes stainless steel or superelastic nickel-titanium wires. The helical band 55 may be constructed of molded flexible plastic, flat wire coil, machined plastic, or other suitable material.

Figure 5B:
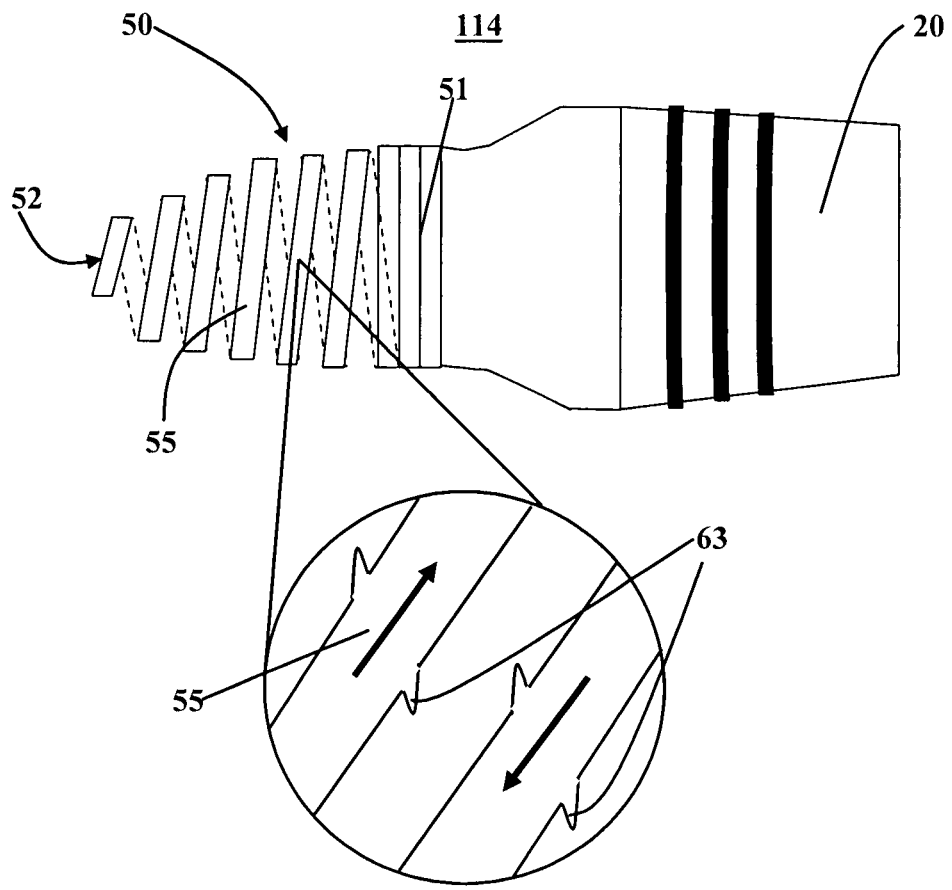
FIG. 5B shows an insert of a zoom view of the ratcheting teeth on the helical band in an unengaged position.
Figure 5C:
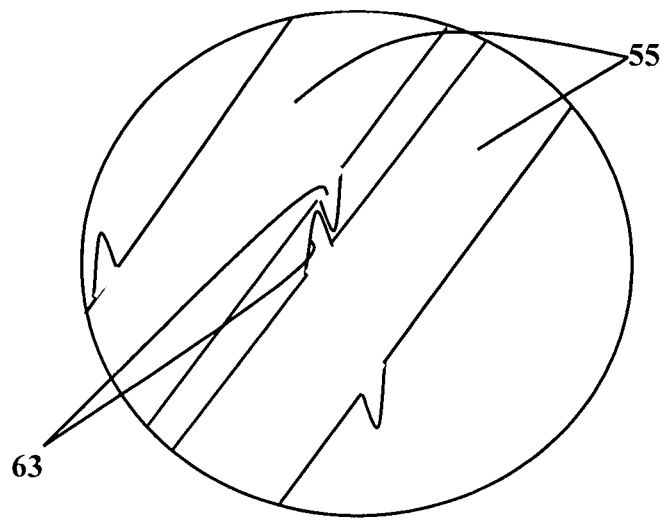
FIG. 5C shows the ratcheting teeth in an engaged position.

Another feature that may be incorporated into the invention is ratcheting teeth 63. As shown in FIGS. 5B and 5C, these teeth 63 are disposed on the lateral edges of the helical band 55 and can temporarily lock the helical band 55 in an enlarged diameter position for ease of placement over the distal end portion 13 of an endoscope. The helical band 55 is unlocked in FIG. 5B. To lock, the helical band 55 is twisted so as to move the band in the direction of the arrows. This movement increases the diameter of the helical band 55. As the helical band 55 is being twisted, the length of the conformable section 50 is simultaneously being compressed so as to move the adjacent coils closer in proximity to one another. Thus, the ratcheting teeth 63 engage as seen in FIG. 5C. The engagement holds the helical band 55 in an open state with a diameter large enough to fit over the distal end portion 13 of an endoscope. The teeth 63 slide past one another and engage each other to prevent loosening of the band 55 once it is expanded. However, after the ligating barrel 114 has been placed over the distal portion end 13 of the endoscope, the teeth 63 may be disengaged by elongating the band 55 axially.

This creates separation between adjacent coils, allowing the teeth 63 to slip past one another in the reverse direction. The helical band 55 can then be retightened to reduce its diameter and close its grip on the outer surface of the endoscope.

Figure 6A:
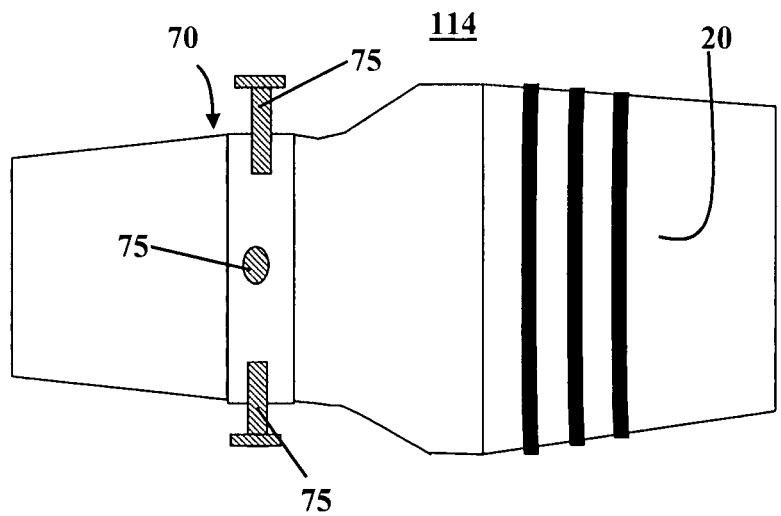
FIG. 6A shows an embodiment of the present invention with screws in the conformable section.
Figure 6B:
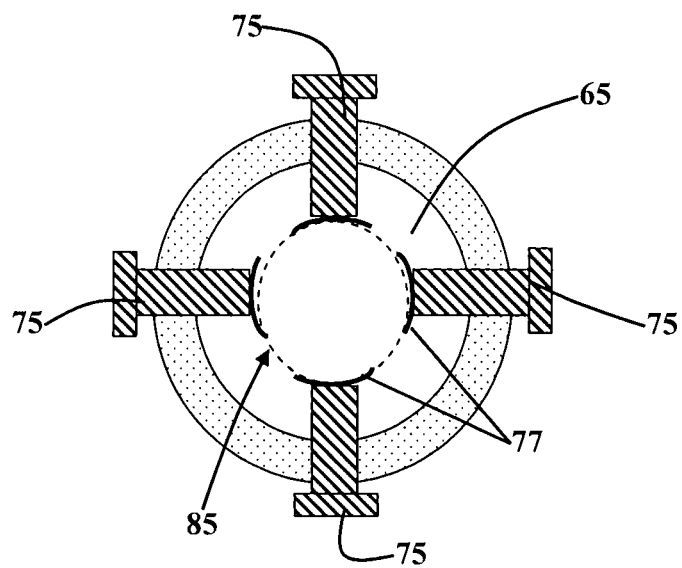
FIG. 6B shows a cross section of the screw placement.

FIGS. 6A and 6B show another embodiment of the present invention. The conformable section 70 comprises a plurality of screws 75 spaced around the circumference of the conformable section 70 configured to engage an endoscope so as to secure the ligating barrel thereto. The screws 75 may be configured with contoured padding 77 to engage the outer surface of an endoscope. Two, three, or four screws 75 can be used in some embodiments. The screws 75 are used to adjust the inner diameter 85 of the conformable section 70. Rotating the screws 75 inward, toward the lumen 65 of the ligating barrel 114 results in a decreased inner diameter 85. Rotating the screws 75 outward from the ligating barrel 114 results in increasing the inner diameter 85. Preferably, the screws 75 are actuated after the ligating barrel 114 has been placed on an endoscope. In another embodiment, the screws 75 can be placed equidistant from each other around the circumference of the conformable section 70. An operator can then actuate the screws 75 accordingly to approximate the diameter of the endoscope and secure a proper fit for the ligating barrel 114. As with all of the embodiments of the present invention, this embodiment may also have internal tabs that prevent the ligating barrel from sliding proximally down the endoscope.

It will, of course, be well understood from the discussions above that other known ligating barrel designs, activation mechanisms, endoscope systems, etc. could be used within the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A ligating barrel for use with an endoscope, the ligating barrel comprising:
    a rigid first tubular section having a lumen extending therethrough, the lumen having a fixed internal diameter, at least two inwardly projecting tabs providing a decreased diameter along a portion of the lumen, the lumen being adapted to contain a distal end of an endoscope, the inwardly projecting tabs being configured to directly engage the distal end of the endoscope when contained within the lumen, and
    a tapered elastomeric second tubular section having an expandable diameter that is expandable from a minimum diameter that is less than the fixed internal diameter of the lumen of the first section, the second section comprising internal ribbing for providing a friction fit and direct contact with the distal end of an endoscope, the internal ribbing comprising a plurality of circumferentially oriented ribs having a semi-circular cross-section and encircling an interior surface of the second section.

2. The ligating barrel of claim 1 wherein said plurality of circumferentially oriented ribs are disposed along the interior surface of the second section at spaced apart locations, the spacing between adjacent ribs being larger than a width of each of the ribs.

3. A ligating barrel adapted to be removably attached to an endoscope, the ligating barrel comprising a tubular band deployment section and a tubular conformable section, said band deployment section having an internal first diameter, said conformable section comprising an internal second diameter and a means for adjusting the internal second diameter of the conformable section for direct attachment to a distal end of an endoscope,
    wherein the distal end of the endoscope comprises an external diameter that is substantially smaller than the first diameter of the band deployment section, and
    wherein the conformable section further comprises a plurality of spaced apart surface features having a curvilinear engagement surface that is configured to frictionally and directly engage the distal end of the endoscope, the surface features each having a width that is less than the spacing therebetween.

4. The ligating barrel of claim 3 wherein said means comprises one of a collet, a flexible helical band, and a plurality of screws.

5. The ligating barrel of claim 3 wherein said means comprises a tapered elastomeric second section having an expandable diameter with internal ribbing for providing a friction fit with the distal end of an endoscope.

6. The ligating barrel of claim 3 further comprising:
    an endoscope having a distal end wherein the ligating barrel is disposed on the distal end of the endoscope.

7. The ligating barrel of claim 6 further comprising an activating component disposed on a proximal portion of the endoscope, the activating component being operably connected to one or more ligating bands disposed about the band deployment section of the ligating barrel.

8. The ligating barrel of claim 7 further comprising an activation line operably connected between the activating component and the ligating barrel.

9. The ligating barrel of claim 7 wherein an activation line is operably connected between the activating component and the one or more bands, the activating line extending through a working channel of the endoscope.

* * * * *

UNITED STATES PATENT AND TRADEMARK OFFICE
CERTIFICATE OF CORRECTION

| | |
|---|---|
| PATENT NO. | : 8,506,477 B2 |
| APPLICATION NO. | : 11/888216 |
| DATED | : August 13, 2013 |
| INVENTOR(S) | : Waller et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 943 days.

Signed and Sealed this
Fourteenth Day of April, 2015

Michelle K. Lee
*Director of the United States Patent and Trademark Office*